United States Patent [19]

Surabian

[11] Plant 4,141

[45] Nov. 1, 1977

[54] NECTARINE TREE

[76] Inventor: Dennis Surabian, P.O. Box 206, Reedley, Calif. 93654

[21] Appl. No.: 755,228

[22] Filed: Dec. 29, 1976

[51] Int. Cl.[2] ..... A01H 5/03

[52] U.S. Cl. ..... Plt./41

[58] Field of Search ..... Plt./41

*Primary Examiner*—Robert E. Bagwill

*Attorney, Agent, or Firm*—Huebner & Worrel

[57] ABSTRACT

A nectarine tree, generally similar to the Fantasia Nectarine Tree (unpatented). which bears yellow fleshed, freestone fruit from fourteen to nineteen days earlier than the Fantasia when grown under the same conditions.

1 Drawing Figures

BACKGROUND OF THE VARIETY

The present invention relates to a new and distinct variety of nectarine tree which is generally similar in tree and fruit to the Fantasia Nectarine Tree (unpatented), the variety of which it is a sport, but which bears fruit which ripens 14 to 19 days earlier than the Fantasia.

The Fantasia Nectarine Tree, developed by the U.S. Department of Agriculture, is well known as a vigorous and productive bearer of yellow fleshed freestone nectarines which are highly colored and of good quality. However, the competition in fresh fruits is acute with wide fluctuations in the market price over a short period under the influence of supply and demand. Thus, the production of high quality fruit when there is little or no competition can be highly profitable, and there is a constant search for sports or mutations which produce high quality fruit earlier or later than other varieties which produce otherwise similar fruit.

ORIGIN AND ASEXUAL REPRODUCTION OF THE NEW VARIETY

My new variety of nectarine tree was discovered by me in June, 1975 as a sport growing in an orchard of Fantasia Nectarine Trees (unpatented) on a ranch which I was and am farming and of which I own an undivided fractional interest. Said ranch is located at the Southeast corner of Frankwood and Sumner Avenues near the City of Reedley, in the County of Fresno, in the State of Calif. Buds from the sport were budded by me on a ranch across the streeet from the ranch where the sport was discovered into Fantasia Nectarine Trees and into Charlie T. Nectarine Trees (a new variety as yet unpatented).

SUMMARY OF THE NEW VARIETY

The instant variety of nectarine tree is characterized by perpetuating the general characteristics of the Fantasia Nectarine Tree, but has the important distinction of ripening from 14 to 19 days earlier. The new nectarine tree is of vigorous growth bearing fruit of large size and generally ovate form having a brilliant yellow (2.5 Y 9/9) background which is mottled to almost solid with moderate (2.5 R 4/10) to dark (2.5 R 3/7) red. The fruit is freestone and has yellow, firm textured flesh.

BRIEF DESCRIPTION OF THE DRAWINGS

The accompanying drawing is a color photograph of four mature fruits of the subject variety, with two of the fruits divided on the suture plane to show the flesh color and the stone, together with a representative twig showing characteristic leaves.

DETAILED DESCRIPTION

Referring more specifically to the pomological details of this new and distinct variety of nectarine tree, the following has been observed under the ecological conditions prevailing in the designated orchards near Reedley, Calif. All major color code plate identifications are by reference to the Nickerson Color Fan of the American Horticultural Council.

TREE

Size: Large.
Vigor: Vigorous.
Figure: Controlled by pruning.
Productivity: Excellent.
Bearing: Regular.
Trunk: Large, smooth and glossy surface.
Branches: Large, smooth surface.
Leaves:
- *Size.*—Large.
- *Length.*—175 mm. average.
- *Width.*—45 mm. average.
- *Shape.*—Lanceolate, apex acuminate.
- *Color.*—Underside moderate yellow green (5 GY 5/6), upperside moderate olive green (5 GY 4/3).
- *Marginal form.*—Serrate.
- *Petiole.*—Length 12 mm., thickness 2 mm.
- *Glandular characteristics.*—One to six, irregularly arranged on petiole and base of leaf, reniform.

Flowers:
- *Dates of bloom.*—March 10 to March 20.
- *Size.*—Normal for nectarine.
- *Color.*—Pink.

FRUIT

Maturity: Fourteen to 19 days before Fantasia.
Size: Large and fairly uniform.
- *Axial diameter.*—65 mm.
- *Transverse in suture plane.*—58 mm.
- *Transverse at right angles to suture plane.*—59 mm.

Form: Generally ovate, but irregular and asymetric.
- *Suture.*—Ventral side — Pronounced with yellow line from apex to stem. Dorsal side — Slight, from apex halfway to edge of stem cavity.
- *Ventral surface.*—Lips unequal.
- *Stem cavity.*—Rounded, 20 mm. diameter, 11 mm. deep.

*Pistil point.*—Usually moderate, but varies from missing to pronounced.

Skin:

*Thickness.*—Normal.

*Tendency to crack.*—None.

*Color.*—Background brilliant yellow (2.5 Y 9/9) mottled to almost solid with red between moderate (2.5 R 4/10) to dark (2.5 R 3/7); pit well: brilliant yellow (2.5 Y 9/9).

*Pubescence.*—None.

Flesh:

*Color.*—Brilliant yellow (2.5 Y 9/9) to moderate orange yellow (10 YR 8/10), lighter around pit cavity with definite lighter streak from pit extending toward suture; surface of pit cavity: strong yellowish pink (5 R 7/9).

*Flavor.*—Good balance between acid and sweet.

*Aroma.*—Pronounced.

*Texture.*—Firm and smooth.

Stone:

*Type.*—Freestone.

*Size.*—Length 35 mm., width 25 mm.

*Form.*—Oval, apex acuminate.

*Ventral edge.*—No wing, medium thickness.

*Dorsal edge.*—No wing, groove shallow base to center, or missing.

*Color.*—Strong red (5 R 4/12) to dark red (5 R 3/7).

Use: Fresh.

Keeping quality: Excellent.

Shipping quality: Excellent.

Although the new variety of nectarine tree possesses the described characteristics as a result of the growing conditions in Fresno County, Calif., in the central portion of the San Joaquin Valley, it is to be understood that variations of the usual magnitude in characteristics incident to growing conditions, fertilization, pruning, and pest control are to be expected.

Having thus described and illustrated my new variety of nectarine tree, what is new and desired to be secured by Letters Patent is:

1. A new and distinct variety of nectarine tree, substantially as illustrated and described, characterized by its vigorous growth; its bearing of large, freestone, yellow fleshed fruit; and by its general resemblance to the Fantasia (unpatented) Nectarine Tree, but from which it is distinguished by its fruit ripening from 14 to 19 days earlier.

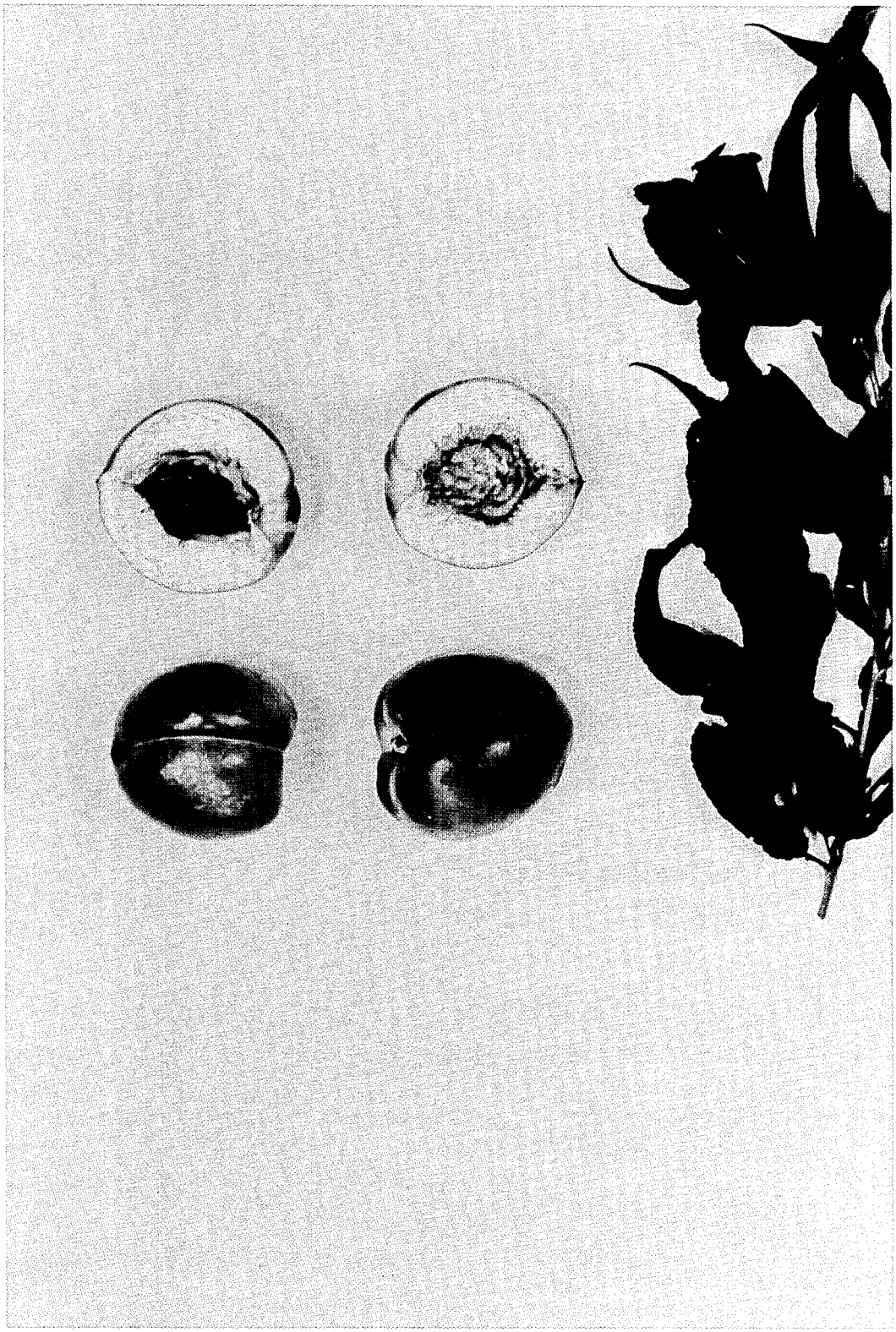

* * * * *